United States Patent [19]

Missbach

[11] Patent Number: 5,491,158
[45] Date of Patent: Feb. 13, 1996

[54] THIOSEMICARBAZONETHIONES

[75] Inventor: Martin Missbach, Rheinfelden, Switzerland

[73] Assignee: Ciba-Geigy Corporation, Ardsley, N.Y.

[21] Appl. No.: 244,081

[22] PCT Filed: Sep. 25, 1993

[86] PCT No.: PCT/EP93/02607

§ 371 Date: May 16, 1994

§ 102(e) Date: May 16, 1994

[87] PCT Pub. No.: WO94/07874

PCT Pub. Date: Apr. 14, 1994

[30] Foreign Application Priority Data

Oct. 6, 1992 [CH] Switzerland ............ 03113/92

[51] Int. Cl.$^6$ ............ C07D 277/54; A61K 31/425
[52] U.S. Cl. ............ 514/369; 548/184
[58] Field of Search ............ 548/184; 514/369

[56] References Cited

U.S. PATENT DOCUMENTS

| | | | |
|---|---|---|---|
| 5,143,928 | 9/1992 | Cetenko | 514/369 |
| 5,208,250 | 5/1993 | Cetenko | 514/369 |
| 5,229,405 | 7/1993 | Feige et al. | 514/369 |

FOREIGN PATENT DOCUMENTS 1301555  12/1972  United Kingdom .

OTHER PUBLICATIONS

Wisenberg et al; Clin Exp Immunol. (1989) 78, 245–249. "Suppression and Augmentation of Rat Adjuvant Arthritis with Monoclonal Anti–Interferon–Gamma Antibody".

Chem Abstract vol. 61, 12008a Corresponding to JP B64 010,345 Jun. 11, 1964.

*Primary Examiner*—Robert Gerstl
*Attorney, Agent, or Firm*—Karen G. Kaiser

[57] ABSTRACT

The invention relates to novel thiosemicarbazonethiones of formula (I) wherein $R_1$ is lower alkyl, lower alk-2-en-1-yl or also lower alk-2-yn-1-yl, $R_2$ and $R_3$ are each independently of the other hydrogen or lower alkyl or, taken together, are lower alkylidene, $R_4$ is hydrogen, lower alkyl, lower alkoxy, aryl or aryl-lower alkyl, $R_5$ is lower alkyl, aryl, aryl-lower alkyl, unsaturated or saturated heterocyclyl-lower alkyl, or is also lower alkyloxycarbonyl-lower alkyl, and the salts thereof, to a process for the preparation of these compounds, to pharmaceutical compositions containing them, and to the use thereof as medicaments.

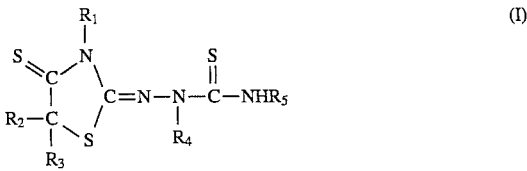

10 Claims, No Drawings

THIOSEMICARBAZONETHIONES

This application is a 371 of PCT/EP93/02607 filed Sep. 25, 1993.

The present invention relates to novel thiosemicarbazonethiones of formula I

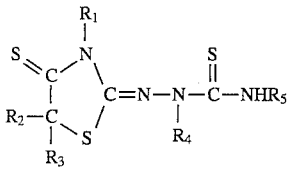

wherein $R_1$ is lower alkyl, lower alk-2-en-1-yl or also lower alk-2-yn-1-yl, $R_2$ and $R_3$ are each independently of the other hydrogen or lower alkyl or, taken together, are lower alkylidene, $R_4$ is hydrogen, lower alkyl, lower alkoxy, aryl or aryl-lower alkyl, $R_5$ is lower alkyl, aryl, aryl-lower alkyl, unsaturated or saturated heterocyclyl-lower alkyl, or is also lower alkyloxycarbonyl-lower alkyl, and the salts thereof, to a process for the preparation of these compounds, to pharmaceutical compositions containing them, and to the use thereof as medicaments.

In this specification, radicals and compounds qualified by the term "lower" will be taken to mean those containing preferably up to and including 7, preferably up to and including 4, carbon atoms.

Lower alk-2-en-1-yl is typically $C_3$–$C_5$alk-2-en-1-yl, preferably allyl or methallyl.

Lower alk-2-yn-1-yl is typically $C_3$–$C_5$alk-2-yn-1-yl, preferably prop-2-yn-1-yl or also but-2-yn-1-yl.

Lower alkyl is $C_1$–$C_4$alkyl, typically methyl, ethyl, propyl or butyl.

Lower alkylidene is typically $C_1$–$C_4$alkylidene, preferably methylene or also ethylidene.

Lower alkoxy is is typically n-propoxy, isopropoxy, n-butoxy or tert-butoxy, preferably ethoxy and, most preferably, methoxy.

Aryl by itself and as moiety of composite radicals such as aryl-lower alkyl is typically phenyl or naphthyl, for example 1- or 2-naphthyl, or substituted phenyl or naphthyl, typically phenyl or naphthyl which are substituted by lower alkyl, halo-lower alkyl, hydroxy, lower alkoxy, lower alkanoyloxy, halogen and/or nitro. Aryl is preferably unsubstituted phenyl or phenyl which is substituted as indicated above, and is most preferably phenyl.

Aryl-lower alkyl is preferably phenyl-lower alkyl and, most preferably, benzyl.

Unsaturated heterocyclyl-lower alkyl is typically heteroaryl-lower alkyl.

Heteroaryl in composite radicals such as heteroaryl-lower alkyl is preferably a monocyclic and also bicyclic or polycyclic heterocyclic radical having aromaticity. Bicyclic and polycyclic heteroaryl may be comprised of a plurality of heterocyclic rings or, preferably, consist of one heterocycle and one or more than one, conveniently one or two and preferably one, fused carbocyclic ring, preferably a benzene ring. Each individual ring typically contains 3, 5, 6 or 7 and, preferably, 5 or 6 ring members. Heteroaryl is preferably an azacyclic, thiacyclic, oxacyclic, thiazacyclic, thiadiazacyclic, oxazacyclic, diazacyclic, triazacyclic and tetrazacyclic radical.

Heteroaryl is most preferably monocyclic monoazacyclic, monothiacyclic or monooxacyclic radicals such as pyrryl, e.g. 2-pyrryl or 3-pyrryl, pyridyl, e.g. 2-, 3- or 4-pyridyl, thienyl, e.g. 2- or 3-thienyl, or furyl, e.g. 2-furyl; bicyclic monoazacyclic, monooxacyclic or monothiacyclic radicals such as indolyl, e.g. 2- or 3-indolyl, quinolinyl, e.g. 2- or 4-quinolinyl, isoquinolinyl, e.g. 1-isoquinolinyl, benzofuranyl, e.g. 2- or 3-benzofuranyl, or benzothienyl, e.g. 2- or 3-benzothienyl; monocyclic diazacyclic, triazacyclic, tetrazacyclic, oxazacyclic, thiazacyclic or thiadiazacyclic radicals such as imidazolyl, e.g. 2-imidazolyl, pyrimidinyl, e.g. 2- or 4-pyrimidinyl, triazolyl, e.g. 1,2,4-triazol-3-yl, tetrazolyl, e.g. 1- or 5-tetrazolyl, oxazolyl, e.g. 2-oxazolyl, isoxazolyl, e.g. 3- or 4-isoxazolyl, thiazolyl, e.g. 2-thiazolyl, isothiazolyl, e.g. 3- or 4-isothiazolyl or 1,2,4- or 1,3,4-thiadiazolyl, e.g. 1,2,4-thiadiazol-3-yl or 1,3,4-thiadiazol-2-yl; or bicyclic diazacyclic, oxazacyclic or thiazacyclic radicals such as benzimidazolyl, e.g. benzimidazolyl, benzoxazolyl, e.g. 2-benzoxazolyl, or benzthiazolyl, e.g. 2-benzthiazolyl.

Heteroaryl radicals are unsubstituted or they carry substituents. Suitable substituents at the ring carbon atoms are typically those cited above in connection with the aryl radicals and, additionally, oxo (=O). Ring nitrogen atoms may be substituted by lower alkyl, aryl-lower alkyl, lower alkanoyl, benzoyl, carboxy, lower alkoxycarbonyl, hydroxy, lower alkoxy, lower alkanoyloxy or oxido ($-\bar{O}|$)

Heteroaryl is preferably pyridyl, thienyl, pyrryl or imidazolyl.

Heteroaryl-lower alkyl is most preferably pyridylmethyl, thienylmethyl, pyrrylmethyl or imidazolylmethyl.

Saturated heterocyclyl-lower alkyl contains a 5- or 6-membered saturated heterocyclic ring which carries a nitrogen or oxygen atom and is preferably an azacyclic or oxacyclic radical which may be substituted or unsubstituted.

A saturated 6-membered heterocyclic ring may contain a nitrogen atom in addition to an oxygen atom.

A saturated 5- or 6-membered heterocyclic radical is conveniently pyrrolidinyl, piperidino, piperidyl, tetrahydrofuranyl or tetrahydropyranyl, wherein one or also more than one hydrogen atom may be replaced by one or more than one substituent, typically by lower alkyl.

A saturated 6-membered heterocyclic radical which also contains a nitrogen atom in addition to an oxygen atom is typically morpholino or also morpholinyl.

Saturated heterocyclyl-lower alkyl is most preferably pyrrolidinylmethyl, tetrahydrofuranylmethyl or also tetrahydropyranylmethyl.

Pharmaceutically acceptable acid addition salts of compounds of formula I are typically their pharmaceutically acceptable salts with suitable mineral acids such as hydrohalic acids, sulfuric acid or phosphoric acid, including hydrochlorides, hydrobromides, sulfates, hydrogensulfates or phosphates, salts with suitable aliphatic or aromatic sulfonic acids or N-substituted sulfamic acids, including methanesulfonates, benzenesulfonates, p-tosylates or N-cyclohexylsulfamates (cyclamates), or salts with strong organic carboxylic acids such as lower alkanecarboxylic acids or unsaturated or hydroxylated aliphatic dicarboxylic acids, including acetates, oxalates, malonates, maleates, fumarates, tartrates or citrates. Salts of compounds of formula I are typically acid addition salts, conveniently their pharmaceutically acceptable salts with suitable mineral acids such as hydrohalic acids. sulfuric acid or phosphoric acid, including hydrochlorides, hydrobromides, sulfates, hydrogensulfates or phosphates, salts with suitable aliphatic or aromatic sulfonic acids or N-substituted sulfamic acids, including methansulfonates, benzenesulfonates, p-tosylates or N-cyclohexylsulfamates (cyclamates).

The compounds of formula I and their pharmaceutically acceptable salts have valuable pharmacological properties. In particular, they have pronounced antiarthritic properties. These properties can be demonstrated in vivo in the adjuvants arthritis model in rats in accordance with the assay of I. Wiesenberg et at. Clin. Exp. Immunol. 78, 245 (1989) in the dosage range from about 0.1 to about 10.0 mg/kg p.o. or i.p., preferably from about 0.1 to abou 3.0 mg/kg p.o. or i.p.

The compounds of formula I and their pharmaceutically acceptable salts can therefore be used for treating diseases of rheumatoid genesis. Such diseases include in particular rheumatoid arthritis, juvenile arthritis, ankylosing spondylitis and other seronegative spondylarthrides, e.g. spondylanhritides in ulceralive coliris and Crohn's disease, and also reactive arthritides, collagen diseases such as lupus erythematosus, degenerative rheumatic diseases, extraarticular rheumatic and pararheumatic diseases such as gout and osteoporosis.

The invention relates in particular to compounds of formula I, wherein $R_1$ is $C_1$–$C_4$alkyl, $C_3$–$C_5$alk-2-en-1-yl or $C_3$–$C_5$alk-2-yn-1-yl, $R_2$ and $R_3$ are each independently of the other hydrogen, identical $C_1$–$C_4$alkyl or $C_1$–$C_4$alkylidene groups, and $R_4$ is hydrogen, $C_1$–$C_4$alkyl, $C_1$–$C_2$alkoxy, phenyl or phenyl-lower alkyl, $R_5$ is $C_1$–$C_4$alkyl, phenyl, naphthyl, phenyl-lower alkyl, pyridyl-lower alkyl, thienyl-lower alkyl, pyrryl-lower alkyl, imidazolyl-lower alkyl, pyrrolidinyl-lower alkyl, tetrahydrofuranyl-lower alkyl or tetrahydropyranyl-lower alkyl or $C_1$–$C_4$alkoxycarbonyl-$C_1$–$C_4$alkyl, and the salts, preferably pharmaceutically acceptable salts, thereof.

More particularly, the invention relates to compounds of formula I, wherein $R_1$ is $C_3$–$C_5$alk-2-en-1-yl, typically allyl or methallyl, or $C_3$–$C_5$alk-2-yn-1-yl, typically prop-2-yn-1-yl, $R_2$ and $R_3$ are both hydrogen or identical $C_1$–$C_4$alkyl groups such as methyl groups, $R_4$ is hydrogen, $C_1$–$C_4$alkyl such as methyl or ethyl, $C_1$–$C_2$alkoxy such as methoxy or ethoxy, phenyl, phenyl-lower alkyl, e.g. benzyl or phenylethyl, and $R_5$ is $C_1$–$C_4$alkyl, e.g. methyl, phenyl, phenyl-lower alkyl,e.g. benzyl or phenylethyl, pyridyl-lower alkyl, thienyl-lower alkyl, pyridyl-lower alkyl, imidazolyl-lower alkyl, pyrrolidinyl-lower alkyl, tetrahydrofuranyl-lower alkyl or tetrahydropyranyl-lower alkyl, e.g. pyridylmethyl, thienylmethyl, pyrrylmethyl, imidazolylmethyl, pyrrolidinylmethyl, tetrahydrofuranylmethyl or tetrahydropyranylmethyl, $C_1$–$C_4$alkoxycarbonyl-$C_1$–$C_4$alkyl, e.g. methoxy- or ethoxycarbonylmethyl or -ethyl, and the salts, preferably pharmaceutically acceptable salts, thereof.

The invention relates very especially to compounds of formula I, wherein $R_1$ is allyl or methallyl, $R_2$ and $R_3$ are both hydrogen and R4 is hydrogen, methyl, or methoxy, and $R_5$ is methyl, phenyl, benzyl, pyridylmethyl or methoxycarbonylmethyl, and the salts, preferably pharmaceutically acceptable salts, thereof.

The invention relates specifically to the compounds of formula I and the salts, preferably pharmaceutically acceptable salts, thereof, named in the Examples.

The compounds of formula I can be prepared in a manner known per se by a) reacting a compound of formula II

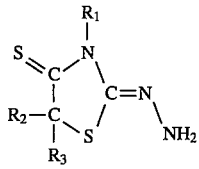

(II)

wherein $R_1$, $R_2$ and $R_3$ are as defined above, with an isothiocyanate of formula III $$R_5\text{—NCS} \qquad (III)$$

The condensation of the compounds of formula II with the compounds of formula III is carried out in known manner in a protic or aprotic solvent, conveniently in an aliphatic halogenated hydrocarbon, as in dichlormethane, preferably methylene chloride, or in an aliphatic or cycloaliphatic ether, e.g. in tetrahydrofuran or also dioxane. Illustrative examples of timber suitable solvents are acetonitrile, ethanol and toluene.

The compounds are reacted in the temperature range from 25° to 120° C., conveniently at the boiling temperature of the solvent in the presence of a basic condensing agent, typically dimethylaminopyridine, triethylamine or pyridine.

The starting compounds of formula II are novel and are prepared by reacting compounds of formula IIa

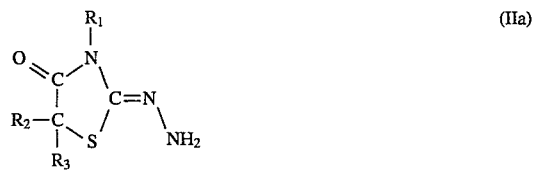

(IIa)

with a sulfurising agent such as phosphorus pentasulfide, Lawesson's reagent (2,4-bis-(methoxyphenyl)-2,4-dithioxo-1,2,3,4,-dithiadiphosphetane) or Yokajama reagent in an inert solvent, preferably in tetrahydrofuran.

The starting materials of formula IIa are known and their preparation is described in DE-OS-2 035 419 and in Swiss patent 511 877.

The isothiocyanates of formula III can be prepared from the corresponding amines of formula IV

$$R_5\text{—NH}_2 \qquad (IV)$$

in which $R_5$ is as defined above, by treatment with thiophosgene.

In a further process variant b) of process a) it is also possible to prepare compounds of formula I by reacting compounds of formula II with a compound of formula V

(V)

wherein $R_5$ is as defined above and $R_6$ is lower alkyl, under the same general condensation conditions as described above in connection with process variant a).

Compounds of formula V are obtained by reacting corresponding amines of formula IV $R_5NH_2$ with carbon disulfide and subsequently with a lower alkyl halide, preferably a lower alkyl chloride.

Compounds of formula I can be prepared by a further process c) by reacting compounds of formula VI

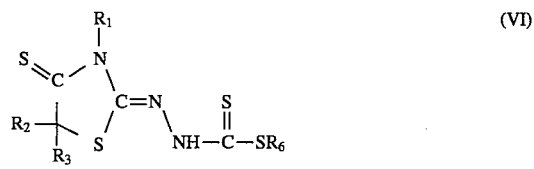

(VI)

in which $R_1$, $R_2$ and $R_3$ are as defined above and $R_6$ is a lower alkyl radical, with corresponding amines of formula IV above

$$R_5\text{—NH}_2 \qquad (IV)$$

wherein $R_5$ is as defined above.

The condensation of the compounds of formula VI with the compounds of formula IV is carried out in known manner in a protic or aprotic solvent, conveniently in an aliphatic halogenated hydrocarbon, as in dichlormethane, preferably methylene chloride, or in an aliphatic or cycloaliphatic ether, e.g. in tetrahydrofuran or also dioxane. Illustrative examples of further suitable solvents are acetonitrile, ethanol and also toluene.

The compounds are reacted in the temperature range from 25° to 120° C., conveniently at the boiling temperature of the solvent in the presence of a basic condensing agent, typically dimethylaminopyridine, triethylamine or also quinoline and pyridine.

The starting compounds of formula VI are novel and can be prepared from the corresponding aforementioned hydrazone of formula II

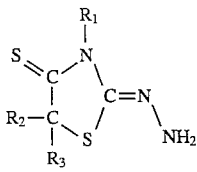
(II)

by reaction with carbon disulfide $CS_2$ and subsequent reaction with a lower alkyl iodide. The reaction of a compound of formula II with carbon disulfide is carded out in the presence of a tertiary organic base, e.g. a tri-lower alkylamine, a Hünig base or an organic nitrogen base, such as pyridine or quinoline. The subsequent reaction with a lower alkyl iodide is carried out by cooling the reaction mixture to a temperature from −10° to +10° C., preferably from 0° to +5° C.

The compounds of formula I can be prepared by a further process d) by reacting compounds of formula VII

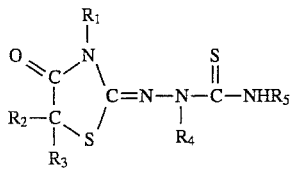
(VII)

with a sulfurising agent.

Suitable sulfurising agents are the aforementioned phosphorus pentasulfide, Lawson's reagent or the Yokajama reagent The reaction with a sulfurising agent is carried out in conventional manner in a protic or aprotic solvent, e.g. an aliphatic or cycloaliphatic ether, e.g. in tetrahydrofuran or dioxane. Further suitable solvents are aliphatic halogenated hydrocarbons such as methylene chloride.

The compounds of formula VII and the sulfurising agent are reacted together in the temperature range from 20° to 120° C., preferably from 60° to 90° C. The preparation of the compounds of formula VII is known and disclosed in DE-OS-2 035 419 and in Swiss patent 511 877.

The process typically comprises reacting a compound of formula IIa with an isothiocyanate of formula III

 NCS (III)

under the same reaction conditions as described in connection with process variant a).

The compounds of formula I obtainable as mixtures of isomers according to process variants a)–d) can, if desired, be separated into the individual isomers and/or a free compound can be converted into a salt or a salt into a free compound or into another salt.

Compounds obtainable by the process of the invention can be converted in conventional amnner intp other compounds of formula I.

Resultant salts can be convened in per se known manner into the free compounds, conveniently by treatment with a base such as an alkali metal hydroxide, a metal carbonate or metal hydrogen carbonate or ammonia, or with another salt-forming base mentioned at the outset or with an acid, conveniently a mineral acid such as hydrochloric acid, or with another salt-forming acid mentioned at the outset.

Salts of compounds of formula I can be convened in a manner known per se into other salts, acid addition salts conveniently by treatment with a suitable metal salt, typically a sodium, barium or silver salt, of another acid in a suitable solvent in which a resultant inorganic salt is insoluble and is thus eliminated from the equilibrium of reaction, and salts of bases by generating the free acid and repeated salt-formation.

The compounds of formula I, including their salts, may also be obtained in the form of hydrates or include the solvent used for crystallisation.

Because of the close relationship between the novel compounds in the free form and in the form of their salts, the references made throughout this specification to the free compounds and their salts will also apply by analogy to the corresponding salts and free compounds.

Racemates can also be separated by known methods into the optical antipodes, conveniently by recrystallisation from an optically active solvent, with the aid of micro-organisms or by reacting the mixture of diastereoisomers or racemate with an optically active compound, e.g. depending on the acid, basic or functionally modifiable groups present in the compound of formula I, with an optically active acid, base or an optically active alcohol, into mixtures of diastereoisomeric salts or functional derivatives such as esters, separating these into the diastereoisomers from which the respective desired enantiomer can be set free in the respective usual manner. Bases, acids or alcohols suitable for the purpose are typically optically active alkaloid bases such as strychine, cinchonine or brucine, or D- or L-(1-phenyl)ethylamine, 3-pipecoline, ephedrine, amphetamine or similar bases which are obtainably by synthesis, optically active carboxylic or sulfonic acids such as quinic acid or D- or L-tartaric acid, D- or L-di-o-toluyltartaric acid, D- or L-malic acid, D- or L-mandelic acid or D- or L-camphorsulfonic acid, or optically active alcohols such as borncol or D- or L-(1-phenyl)ethanol.

The invention relates also to those embodiments of the process in which a compound obtainable as intermediate in any stage of the process is used as starting material and the remaining steps are carried out, or a starting material is used in the form of a derivative or a salt or, especially, is formed under the reaction conditions.

The invention also relates to the novel starting materials which have been specially developed for the preparation of the novel compounds, especially those which result in the compounds of formula I described at the beginning as being especially preferred, to processes for their preparation and to the use thereof as intermediates.

The pharmaceutical compositions of this invention which contain the novel compound or a pharmaceutically acceptable salt thereof are those for enteral, e.g. oral, and also rectal and parenteral administration to warm-blooded animals, and they contain the pharmacologically active compound alone or together with a pharmaceutically acceptable carrier. The daily dose will depend on the age, sex and individual condition of the patient as well as on the mode of administration.

The novel pharmaceutical compositions contain from about 10 to 80 %, preferably from about 20 to 60 %, of the active compound. Pharmaceutical compositions for enteral or parenteral administration are typically those in dosage unit forms such as dragées, tablets, capsules or suppositories, and also ampoules. These dosage forms are prepared in a manner known per se, typically by conventional mixing, granulating, confectioning, dissolving or lyophilising methods. Pharmaceutical compositions for oral administration can typically be prepared by combining the the active compound with solid carriers, granulating the mixture so obtained and, if desired or necessary, processing the mixture or granulate, after addition of suitable excipients, to tablets or dragée cores.

Suitable careers are especially fillers such as sugars, conveniently lactose, saccharose, mannitol or sorbitol, cellulose preparations and/or calcium phosphates, typically tricalcium phosphate or calcium hydrogen phosphate, and also binders such as starch pastes, conveniently using maize, corn, flee or potato starch, gelatin, tragacanth, methyl cellulose and/or polyvinyl pyrrolidone, and/or, if desired, disintegrators such as the above-mentioned starches, also carboxymethyl starch, crosslinked polyvinylpyrrolidone, agar, alginic acid or a salt thereof such as sodium alginate. Excipients are in particular gildants, flow control agents and lubricants, conveniently silica, talcum, stearic acid or salts thereof, typically magnesium stearate or calcium stearate, and/or polyethylene glycol. Dragée cores can be provided with suitable non-enteric or enteric coatings, typically using concentrated sugar solutions which may contain gum arabic, talcum, polyvinylpyrrolidone, polyethylene glycol and/or titanium dioxide, shellac solutions in suitable organic solvents or mixtures of solvents or, for the preparation of enteric coatings, solutions of suitable cellulose preparations such as acetyl cellulose phthalate or hydroxypropyl methyl cellulose phthalate. Dyes or pigments can be added to the tablets or dragée coatings, conveniently to identify or indicate different doses of active compound.

Further pharmaceutical compositions for oral administration are dry-filled capsules made of gelatin and also soft-sealed capsules consisting of gelatin and a plasticiser such as glycerol or sorbitol. The dry-filled capsules can contain the active ingredient in the form of granules, conveniently in admixture with fillers such as lactose, binders such as starches, and/or glidants such as talcum or magnesium stearate, and with or without stabilisers. In soft capsules, the active ingredient is preferably dissolved or suspended in a suitable liquid, typically a fatty oil, paraffin oil or a liquid polyethylene glycol, to which a stabiliser can also be added.

Suitable pharmaceutical compositions for rectal administration are typically suppositories, which consist of a combination of the active compound with a suppository base. Examples of suitable suppository bases are natural or synthetic triglycerides, paraffin hydrocarbons, polyethylene glycols and higher alkanols. It is also possible to use gelatin capsules for rectal administration that contain a combination of the active compound with a base substance. Suitable base substances are typically liquid triglycerides, polyethylene glycol or paraffin hydrocarbons.

Compositions for parenteral administration are preferred, conveniently in the form of aqueous solutions or suspensions of the active compound, for example oily injection suspensions using suitable lipophilic solvents or vehicles such as fatty oils, typically sesame oil, or synthetic fatty acid esters such as ethyl oleate or triglycerides, or aqueous injection suspensions which may contain viscosity increasing substances, conveniently sodium carboxymethyl cellulose, sorbitol and/or dextran, and also with or without stabilisers.

The invention also relates to the use of the compound of formula I, preferably in the form of pharmaceutical compositions. The dosage of the active compound will depend on the species of the warm-blooded animal, on the age and individual condition of the patient, and also on the mode of application. The contemplated daily dosage for parenteral administration to a patient of approximately 75 kg body weight will normally be from about 5 mg to 1000 mg/kg, preferably from about 10 mg to 200 mg. This dose can be administered in a single dose or in several individual doses, typically from 2 to 4 doses. Thus pharmaceutical compositions in dosage unit form contain from about 5 mg to 250 mg, preferably from about 10 mg to 50 mg, of active compound.

The invention is illustrated in more detail by the following non-limitative Examples. Pressures are given in mbar.

EXAMPLE 1

1.0 g of 1-(3-allyl-4-oxothiazolidin-2-ylidene)-4-phenylthiosemicarbazone and 1.5 g of Lawesson's reagent are refluxed for 5 hours in 25 ml of tetrahydrofuran as solvent. The mixture is cooled to room temperature and the solvent stripped off on a rotary evaporator. The crude product is taken up in a minor amount of methylene chloride and chromatographed on silica gel with methylene chloride as eluant. After recrystallisation from methylene chloride/ether, the crystalline product is isolated by filtration and dried under a high vacuum, giving solid 1-(3-allyl-4-thiothiazolidin-2-ylidene)-4-phenylthiosemicarbazone with a melting point of 155°–157° C.

EXAMPLE 2

Following the general procedure described in Example 1, 0.5 g of 1-(3-allyl-4-oxothiazolidin-2-ylidene)-4-(thiophene-2-methyl)thiosemicarbazone and 0.62 g of Lawesson's reagent are refluxed for 6 hours in 20 ml of tetrahydrofuran. After chromatography as described in Example 1, the product is recrystallised from methylene chloride/ether to give crystals of 1-(3-allyl-4-thiothiazolidin-2-ylidene)-4-(thiophene-2-methyl)thiosemicarbazone with a melting point of 144°–145° C.

EXAMPLE 3

Following the general procedure described in Example 1, 0.7 g of 1-(3-allyl-4-oxothiazolidin-2-ylidene)-4-(tetrahydrofuran-2-methyl)thiosemicarbazone and 0.9 g of Lawesson's reagent are refluxed for 6 hours in 20 ml of tetrahydrofuran. After chromatography as described in Example 1, the product is recrystallised from methylene chloride/ether to give crystals of 1-(3-allyl-4-thiothiazolidin-2-ylidene)-4-(tetrahydrofuran-2-methyl)thiosemicarbazone with a melting point of 149°–150° C.

EXAMPLE 4

Following the general procedure described in Example 1, 1.2 g of 1-(3-allyl-4-oxothiazolidin-2-ylidene)-4-methylthiosemicarbazone and 1.5 g of Lawesson's reagent are refluxed for 6 hours in 20 ml of tetrahydrofuran. After chromatography as described in Example 1, the product is recrystallised from methylene chloride/ether to give crystals of 1-(3-allyl-4-thiothiazolidin-2-ylidene)-4-methylthiosemicarbazone with a melting point of 165°–166° C.

EXAMPLE 5

Following the general procedure described in Example 1, 0.7 g of 1-(3-propynyl-4-oxothiazolidin-2-ylidene)-4-methylthiosemicarbazone 1.0 g of Lawesson's reagent are refluxed for 8 hours in 30 ml of tetrahydrofuran. After chromatography as described in Example 1, the product is recrystallised from methylene chloride/ether to give crystals of 1-(3-propynyl-4-thiothiazolidin-2-ylidene)-4-methylthiosemicarbazone with a melting point of 180° C.

EXAMPLE 6

Following the general procedure described in Example 1, 0.5 g of 1-(3-allyl-4-oxothiazolidin-2-ylidene)-4-allylthiosemicarbazone and 0.75 g of Lawesson's reagent are refluxed for 8 hours in 50 ml of tetrahydrofuran. After chromatography as described in Example 1, the product is recrystallised from methylene chloride/ether to give crystals of 1-(3-allyl-4-thiothiazolidin-2-ylidene )-4-allylthiosemicarbazone with a melting point of 115° C.

What is claimed is:

1. A compound of formula I,

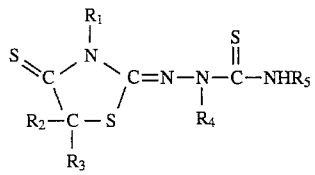

wherein $R_1$ is $C_1$–$C_4$alkyl, $C_3$–$C_5$alk-2-en-1-yl or $C_3$–$C_5$alk-2-yn-1-yl, $R_2$ and $R_3$ are each independently of the other hydrogen, identical $C_1$–$C_4$alkyl or $C_1$–$C_4$alkylidene groups, and $R_4$ is hydrogen, $C_1$–$C_4$alkyl, $C_1$–$C_2$alkoxy, phenyl or phenyl-lower alkyl, $R_5$ is $C_1$–$C_4$alkyl, phenyl, naphthyl, phenyl-lower alkyl, pyridyl-lower alkyl, thienyl-lower alkyl, pyrryl-lower alkyl, imidazolyl-lower alkyl, pyrrolidinyl-lower alkyl, tetrahydrofuranyl-lower alkyl or tetrahydropyranyl-lower alkyl or $C_1$–$C_4$alkoxycarbonyl-$C_1$–$C_4$alkyl, or a pharmaceutically acceptable salt thereof.

2. A compound according to claim 1 of formula I, wherein $R_1$ is $C_3$–$C_5$alk-2-yn-1-yl such as allyl or methallyl, or $C_3$–$C_5$alk-2-yn-1-yl such as prop-2-yn-1-yl, $R_2$ and $R_3$ are both hydrogen or identical $C_1$–$C_4$alkyl groups such as methyl groups, $R_4$ is hydrogen, $C_1$–$C_4$alkyl such as methyl or ethyl, $C_1$–$C_2$alkoxy such as methoxy or ethoxy, phenyl, phenyl-lower alkyl, e.g. benzyl or phenylethyl, and $R_5$ is $C_1$–$C_4$alkyl, e.g. methyl, phenyl, phenyl-lower alkyl, e.g. benzyl or phenylethyl, pyridyl-lower alkyl, thienyl-lower alkyl, pyridyl-lower alkyl, imidazolyl-lower alkyl, pyrrolidinyl-lower alkyl, tetrahydrofuranyl-lower alkyl or tetrahydropyranyl-lower alkyl, e.g. pyridylmethyl, thienylmethyl, pyrrylmethyl, imidazolylmethyl, pyrrolidinylmethyl, tetrahydrofuranylmethyl or tetrahydropyranylmethyl, $C_1$–$C_4$alkoxycarbonyl-$C_1$–$C_4$alkyl, e.g. methoxy- or ethoxycarbonylmethyl or -ethyl, or a pharmaceutically acceptable salt thereof.

3. A compound according to claim 1 of formula I, wherein $R_1$ is allyl or methallyl, $R_2$ and $R_3$ are both hydrogen and $R_4$ is hydrogen, methyl or methoxy, and $R_5$ is methyl, phenyl, benzyl, pyridylmethyl or methoxycarbonylmethyl, or a pharmaceutically acceptable salt thereof.

4. 1-3(Allyl-4-thiothiazolidin-2-ylidene)-4-phenylthiosemicarbazone or a pharmaceutically acceptable salt thereof according to claim 1.

5. 1-(3-Allyl-4-thiothiazolidin-2-ylidene)-4-(thiophene-2-methyl)thiosemicarbazone or a pharmaceutically acceptable salt thereof according to claim 1.

6. 1-(3-Allyl-4-thiothiazolidin-2-ylidene)-4-(tetrahydrofuran-2-methyl)thiosemicarbazone or a pharmaceutically acceptable salt thereof according to claim 1.

7. 1-(3-Allyl-4-thiothiazolidin-2-ylidene)-4-methylthiosemicarbazone or a pharmaceutically acceptable salt thereof according to claim 1.

8. 1-(3-Propynyl-4-thiothiazolidin-2-ylidene)-4-methylthiosemicarbazone or a pharmaceutically acceptable salt thereof according to claim 1.

9. 1-(3-Allyl-4-thiothiazolidin-2-ylidene)-4-allylthiosemicarbazone or a pharmaceutically acceptable salt thereof.

10. A pharmaceutical composition comprising, in addition to at least one customary pharmaceutical excipient, a compound according to claim 1 in the free form or in the form of a pharmaceutically acceptable salt as active ingredient.

* * * * *